(12) United States Patent
Tatarinova

(10) Patent No.: US 8,222,388 B2
(45) Date of Patent: Jul. 17, 2012

(54) BROADLY EXPRESSING REGULATORY REGIONS

(75) Inventor: Tatiana Tatarinova, Los Angeles, CA (US)

(73) Assignee: Ceres, Inc., Thousand Oaks, CA (US)

( * ) Notice: Subject to any disclaimer, the term of this patent is extended or adjusted under 35 U.S.C. 154(b) by 179 days.

(21) Appl. No.: 12/515,930

(22) PCT Filed: Nov. 16, 2007

(86) PCT No.: PCT/US2007/084997
§ 371 (c)(1),
(2), (4) Date: Dec. 15, 2009

(87) PCT Pub. No.: WO2008/064128
PCT Pub. Date: May 29, 2008

(65) Prior Publication Data
US 2010/0107275 A1    Apr. 29, 2010

Related U.S. Application Data

(60) Provisional application No. 60/860,626, filed on Nov. 22, 2006.

(51) Int. Cl.
| C12N 15/113 | (2010.01) |
| C12N 15/82 | (2006.01) |
| C12N 15/09 | (2006.01) |
| C12N 15/00 | (2006.01) |
| A01H 5/00 | (2006.01) |

(52) U.S. Cl. .................. 536/24.1; 536/23.1; 435/320.1; 435/468; 800/287; 800/278; 800/295

(58) Field of Classification Search .......................... None
See application file for complete search history.

(56) References Cited

U.S. PATENT DOCUMENTS

| | | | |
|---|---|---|---|
| 4,987,071 A | 1/1991 | Cech et al. | |
| 5,034,323 A | 7/1991 | Jorgensen et al. | |
| 5,204,253 A | 4/1993 | Sanford et al. | |
| 5,231,020 A | 7/1993 | Jorgensen et al. | |
| 5,254,678 A | 10/1993 | Haseloff et al. | |
| 5,538,880 A | 7/1996 | Lundquist et al. | |
| 5,591,616 A | 1/1997 | Hiei et al. | |
| 5,808,034 A | 9/1998 | Bridges et al. | |
| 6,037,524 A * | 3/2000 | Greenland et al. ............ 800/287 |
| 6,245,969 B1 | 6/2001 | Chory et al. | |
| 6,252,139 B1 | 6/2001 | Doerner et al. | |
| 6,326,527 B1 | 12/2001 | Kirihara et al. | |
| 6,329,571 B1 | 12/2001 | Hiei | |
| 6,423,885 B1 | 7/2002 | Waterhouse et al. | |
| 6,452,067 B1 | 9/2002 | Bedbrook et al. | |
| 6,455,760 B1 | 9/2002 | Zhao et al. | |
| 6,573,099 B2 | 6/2003 | Graham | |
| 6,683,230 B1 | 1/2004 | Jepson et al. | |
| 6,696,623 B1 | 2/2004 | Doerner et al. | |
| 6,753,139 B1 | 6/2004 | Baulcombe et al. | |
| 6,765,085 B2 | 7/2004 | Chory et al. | |
| 6,777,588 B2 | 8/2004 | Waterhouse et al. | |
| 6,987,025 B1 | 1/2006 | Azpiroz et al. | |
| 2003/0150026 A1 | 8/2003 | Chory et al. | |
| 2003/0175783 A1 | 9/2003 | Waterhouse et al. | |
| 2003/0175965 A1 | 9/2003 | Lowe et al. | |
| 2003/0180945 A1 | 9/2003 | Wang et al. | |
| 2004/0139501 A1 * | 7/2004 | Hauptmann et al. .......... 800/287 |
| 2004/0214330 A1 | 10/2004 | Waterhouse et al. | |
| 2005/0132432 A1 | 6/2005 | Haseloff et al. | |
| 2006/0021089 A1 | 1/2006 | Fang et al. | |
| 2006/0057724 A1 | 3/2006 | Alexandrov et al. | |
| 2006/0162020 A1 | 7/2006 | Sauer et al. | |
| 2006/0168695 A1 | 7/2006 | Klebsattel et al. | |

FOREIGN PATENT DOCUMENTS

| | | |
|---|---|---|
| WO | 96/32488 | 10/1996 |
| WO | 97/01952 | 1/1997 |
| WO | 98/36083 | 8/1998 |
| WO | 98/53083 | 11/1998 |
| WO | 99/32619 | 7/1999 |
| WO | 02/46449 | 6/2002 |

OTHER PUBLICATIONS

Federspiel et al 1999 GenBank Accession AC009525, alignment provided in office action.*
Federspiel et al 1999 GenBank Accession AC009894, alignment provided in office action.*
Bechtold et al., "In planta Agrobacterium mediated gene transfer by infiltration of adult *Arabidopsis thaliana* plants" *C.R. Acad. Sci. Paris*, 316:1194-1199 (1993).
Chenna et al., "Multiple sequence alignment with the Clustal series of programs" *Nucleic Acids Res.*, 31(13):3497-3500 (2003).
de Feyter and Gaudron, Methods in Molecular Biology, vol. 74, Chapter 43, "Expressing Ribozymes in Plants", Edited by Turner, P.C., *Humana Press Inc.*, Totowa, NJ, 1997, pp. 403-415.
Guatelli et al., Isothermal, in vitro amplification of nucleic acids by multienzyme reaction modeled after retroviral replication, *Proc. Natl. Acad. Sci USA*, 1990, 87: 1874-1878.
He and Gan, "A gene encoding an acyl hydrolase is involved in leaf senescence in *Arabidopsis*," *Plant Cell*, 2002, 14(4): 805-815.
Hyrup et al., Peptide nucleic acids (PNA): synthesis, properties and potential applications *Bioorgan. Med. Chem.*, 4:5-23 (1996).
Lewis, "PCR's competitors are alive and well and moving rapidly towards commercialization," *Genetic Engineering News*, 1992, 12(9):1.
Perriman et al., "Effective ribozyme delivery in plant cells" Proc. Natl. Acad. Sci. USA, 92(13):6175-6179 (1995).
Summerton and Weller, "Morpholino antisense oligomers: design, preparation, and properties" *Antisense Nucleic Acid Drug Dev.*, 7:187-195 (1997).
Tanabe et al., "A novel cytochrome P450 is implicated in brassinosteroid biosynthesis via the characterization of a rice dwarf mutant, dwarf11, which reduced seed length," *Plant Cell*, 2005, 17: 776-790.
Weiss, "Hot prospect for new gene amplifier," *Science*, 1991, 254: 1292-1293.
Yan et al., "New construct approaches for efficient gene silencing in plants," *Plant Physiology*, 2006, 141: 1508-1518.

* cited by examiner

*Primary Examiner* — Brent T Page
(74) *Attorney, Agent, or Firm* — Fish & Richardson P.C.

(57) ABSTRACT

Regulatory regions suitable for directing expression of a heterologous polynucleotide in plant tissues, e.g., flower and silique tissues, are described, as well as nucleic acid constructs that include these regulatory regions. Also disclosed are transgenic plants that contain such constructs and methods of producing such transgenic plants.

8 Claims, No Drawings

SEQUENCE LISTING

```
<160> NUMBER OF SEQ ID NOS: 3

<210> SEQ ID NO 1
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Predicted sequence for Promoter PD1466

<400> SEQUENCE: 1
atttaggtgt taaatctgat aatttaggtt tgaataagtt gtatatttgt ttctttgatt      60
aaaaaaagaa cctatatata tacaaaaata aataaaaagt tctagatttc aattttccgt     120
atatagcggg ttgaattgtc tattttaata tgaaaattga cggatcttat aaacaaaatg     180
ttctgaaata tgtaaaagga tttagccaaa gttaaccaaa aaaaaaaaac aaacagaaaa     240
gtcacattca catgtcgtgg tagatctaag gcattaattt agaaatatgt cgttacaata     300
agcggagaac atgggacgtt tctcgtggtc caatcagacg aacgagatct cataaattaa     360
atgacttcag acgagggaat tcatggcaga atgataatgc aacttaagtg actttagagt     420
gaaaatgata cgagaacaat gcataatcca tatgaccgtt gagtgagtga taccattagc     480
gcgatacaag cgggactata aactgatcta gattgttttt cttgggaaaa aatgttacaa     540
attttaaata tgtagtttga attgttaaac caagattcaa cagaaatata ccgtaaataa     600
```

```
acaacagttg ataatagtca tcgaaaagat atcaactgat tcttcacttg ggctactgtg    660
acggcccgtt aggggttctca atataagtca taactacga tctacgattc actgaaacaa    720
ataaaacaca gccacgtgtc caccctccca catcaccgtc cgatctaacc cacgacaagc    780
ttacaacacg ggtcataccg ctcgtgcagc gtgttccgtc atccacggga ttacaacttc    840
taccagatcc accaaaccct caaaacaatc tgaaccgttc atttcatttt gacctcatct    900
atatattctc tgtcactccc tttctcttct cctcgcacac acttctctct ctctctctct    960
ctgcctcctt tcggattcaa atctcagatc tagctcaacc                         1000
```

<210> SEQ ID NO 2
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Predicted sequence for Promoter PD1468

<400> SEQUENCE: 2

```
ctttctaagt ggcaaaatat ctctttcata aaaaaaaaag gaaagaataa taaataaaaa     60
tatctctttc attctaactt ggcattaaaa tttagcaaaa actatttgtg gaacttgaaa    120
aaaatattac tagctcagac ttaaacttaa atagtaacaa gcatattaaa agtcatgcta    180
actgagatat tgatttcctc atctcaagaa actatcttat gaatctgttt ccgattattt    240
tagtttccca tcaatcatct ttaatttcta ggaagtttga tttttttgaaa atttctccac    300 ctgcttaaat ttcattacaa tttttaatct tagataaaca actgtaattt atgcaaaatg    360
aactgattat ataagtcgtt atgaatattt atatttttta aaaacatttc agcaaaactg    420
atatactttt tttttttttt ttttttgcaag caaataaaca aacttccttg aataaaacgt    480
gaaaaataat aagagtcttt aaagataaac gttgttcata tacattacgt catataaat     540 atataacaat taagacaata caaacatata tacaattctc attgggttga acattataa     600 agataagata aacatctgta tatatacatt ggtatacaat attttttcata aatttttttt    660 tctctaatcg acagttatat atatacagaa ccataatttt taaagcatgc tttccaatgc    720
gttttttttt tttttttttt tttttgtaaa ccaaagccgt gtttctaaac ctcaatttat    780
aaatttggtg tagcttttca accttgatga aattattaca tagaatcatt cgttaaaga    840 cttataattg ggtttagaaa agcccatttt aaatttaaag cccaatatac tgctcgaaaa    900
ggaggaaacc ctagaaacat tgtggtatat aaattctttt cgtctcgttc gctaatcagt    960
tctccgccac accaatctcc agaaaagggg agaagcaaaa                         1000
```

<210> SEQ ID NO 3
<211> LENGTH: 997
<212> TYPE: DNA
<213> ORGANISM: Arabidopsis thaliana
<220> FEATURE:
<221> NAME/KEY: misc_feature
<222> LOCATION: (1)..(997)
<223> OTHER INFORMATION: Sequence for Promoter PD1485

<400> SEQUENCE: 3

```
tagataacgg aaacaagatt aatgtatcat cattcattcc ttgttgattt aattaaacag     60
atgaacaaat gatatgtaat aataaggtct cggtttacag tgaaagtgat ttaatttagt    120
atctttgtta cttcgattat tgaattgagc gtgtgtactt atgaagatta aatcgatgat    180
gcatgggctc ctgaagatta aaaaactcaa tagacactta accagaatta atgatattgg    240
```

-continued

```
cccgatgagt attggcccat taaggcccat taagagagcg aaaaccctaa acgagaaaca    300
agggatatac tcagagcatc ttccttggtt actatataat aagctttagg ctgctagatg    360
cctgcctcct tgcacctctt ttctttctct cgttctcatc tttctctcta aggttagtcc    420
cttgtgtaga tcctctcttc atcgattcaa tttcatcttc cttggtttga tttaggaatt    480
ttgtcacgat ttggtgttta gatgatggag tcttgctgtt gatctatgtt tatagcactt    540
tgtttccatg gttctgttgt ttcttaccgt tgttgtgca tcgatctggt tttggtagat     600
ccctcgtaga taataatctg aatatgtcaa agttttctta caagtctgtt gtgttttcag    660
ttttgattga tattgttatc catgtagtag tcgatcatcc aaaaactggt tcagtgtgat    720
tctccgatca tcgccgctga ttttatattt atcatcaggt atagatttgc aggttttatt    780
gtgttcgttg tgtgttttttg ttctttgtta aatttaacct ctatgcattt gatgtacatg   840
tttttgtgtt ggtctcagtt tctcttattc tgtataagct aagctaaagt ctccatggtt    900
agtgtctgtt tagtattaaa atatttcaat ttgctaattc tttatgtttt tgtgatgata    960
ttgcagagat tttgtaggtg acaatcaaaa gtttgac                             997
```

BROADLY EXPRESSING REGULATORY REGIONS

CROSS-REFERENCE TO RELATED APPLICATION

This application is a National Stage application under 35 U.S.C. §371 and claims the benefit of International Application No. PCT/US2007/084997, having an International Filing Date of Nov. 16, 2007, which claims the benefit of priority of the U.S. Provisional Application Ser. No. 60/860,626, having a filing date of Nov. 22, 2006, all of which are incorporated herein in their entirety.

TECHNICAL FIELD

This document relates to methods and materials involved in regulating gene expression in eukaryotic organisms (e.g., plants).

BACKGROUND

An essential element for genetic engineering of plants is the ability to express genes using various regulatory regions. The expression pattern of a transgene, conferred by a regulatory region, is critical for the timing, location, and conditions under which a transgene is expressed, as well as the intensity with which the transgene is expressed in a transgenic plant. Having the ability to modulate the pattern and level of expression of a transgene can allow plants with desired characteristics or traits to be generated. There is a continuing need for suitable regulatory regions that can facilitate transcription of sequences that are operably linked to the regulatory region.

SUMMARY

This document provides materials and methods involving regulatory regions having the ability to direct transcription in eukaryotic organisms (e.g., plants). For example, this document provides regulatory regions having the ability to direct transcription in various plant tissues, such as flower and silique tissues. Also provided herein are nucleic acid constructs, plant cells, and plants containing such regulatory regions, and methods of using such regulatory regions to express polynucleotides in plants and to alter the phenotype of plant cells. Regulatory regions that direct transcription broadly in various tissues of a plant can be used, for example, to modulate (e.g., increase or decrease) the resistance of the plant to stress, pathogens, herbicides, or antibiotics; to modulate plant architecture, organ size or organ number; or to modulate nutrient utilization or synthesis of proteins, hormones, oils, sugars, or other compounds in the plant.

In one aspect, an isolated nucleic acid is provided. The isolated nucleic acid comprises a regulatory region having 80 percent or greater sequence identity to the polynucleotide sequence set forth in SEQ ID NO:1, where the regulatory region directs transcription of an operably linked heterologous polynucleotide in a tissue selected from the group consisting of flower, silique, and stem tissue.

In another aspect, an isolated nucleic acid is provided. The isolated nucleic acid comprises a regulatory region having 80 percent or greater sequence identity to the polynucleotide sequence set forth in SEQ ID NO:2, where the regulatory region directs transcription of an operably linked heterologous polynucleotide in a tissue selected from the group consisting of flower, silique, and root tissue.

In another aspect, an isolated nucleic acid is provided. The isolated nucleic acid comprises a regulatory region having 80 percent or greater sequence identity to the polynucleotide sequence set forth in SEQ ID NO:3, where the regulatory region directs transcription of an operably linked heterologous polynucleotide in a tissue selected from the group consisting of flower and silique tissue.

The sequence identity can be 90 percent or greater. The nucleic acid can comprise a regulatory region having a nucleotide sequence corresponding to SEQ ID NO:1. The nucleic acid can comprise a regulatory region having a nucleotide sequence corresponding to SEQ ID NO:2. The nucleic acid can comprise a regulatory region having a nucleotide sequence corresponding to SEQ ID NO:3.

In another aspect, a nucleic acid construct is provided. The nucleic acid construct comprises any of the nucleic acids described above operably linked to a heterologous polynucleotide. The heterologous polynucleotide can comprise a polynucleotide sequence encoding a polypeptide. The heterologous polynucleotide can be in an antisense orientation relative to the regulatory region. The heterologous polynucleotide can be transcribed into an RNA that inhibits expression of a gene.

In another aspect, a transgenic plant or plant cell is provided. The transgenic plant or plant cell can be transformed with any of the nucleic acids described above.

In another aspect, a method of producing a transgenic plant is provided. The method comprises (a) introducing into a plant cell an isolated polynucleotide comprising any of the nucleic acids described above, and (b) growing a plant from the plant cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

The invention features isolated nucleic acids comprising regulatory regions. The terms "nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded, i.e., a sense strand or an antisense strand. Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An isolated nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences, e.g., a chemically synthesized nucleic acid, or a cDNA or genomic DNA fragment produced by the polymerase chain reaction (PCR) or restriction endonuclease treatment. An isolated nucleic acid also refers to a DNA molecule that is incorporated into a vector, an autonomously replicating plasmid, or a virus, or transformed into the genome of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Regulatory Regions

A regulatory region described herein is a nucleic acid that can direct transcription when the regulatory region is operably linked 5' to a heterologous nucleic acid. If a regulatory region described herein is a naturally occurring nucleic acid, "heterologous nucleic acid" refers to a nucleic acid other than the naturally occurring coding sequence to which the regulatory region was operably linked in a plant. With regard to one regulatory region provided herein, PD1466 (SEQ ID NO:1), a heterologous nucleic acid is a nucleic acid other than the coding sequence for the S-adenosyl-L-homocysteine hydrolase polypeptide of *Arabidopsis*. With regard to another regulatory region provided herein, PD1468 (SEQ ID NO:2), a heterologous nucleic acid is a nucleic acid other than the coding sequence for the 60S ribosomal protein L19 (RPL19A) polypeptide of *Arabidopsis*. With regard to another regulatory region provided herein, PD1485 (SEQ ID NO:3), a heterologous nucleic acid is a nucleic acid other than the coding sequence for the putative elongation factor 2 polypeptide of *Arabidopsis*. If a regulatory region described herein is not a naturally occurring nucleic acid, "heterologous nucleic acid" refers to any transcribable nucleic acid. The term "operably linked" refers to positioning of a regulatory region and a transcribable sequence in a nucleic acid so as to allow or facilitate transcription of the transcribable sequence. For example, a regulatory region is operably linked to a coding sequence when RNA polymerase is able to transcribe the coding sequence into mRNA, which then can be translated into a protein encoded by the coding sequence.

Regulatory regions can include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, and introns.

The nucleic acid sequences set forth in SEQ ID NOs:1-3 are examples of regulatory regions provided herein. However, a regulatory region can have a nucleotide sequence that deviates from that set forth in SEQ ID NO:1, SEQ ID NO:2, or SEQ ID NO:3, while retaining the ability to direct expression of an operably linked nucleic acid. For example, a regulatory region having 80% or greater (e.g., 81% or greater, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater) sequence identity to the nucleotide sequence set forth in SEQ ID NO:1, SEQ ID NO:2, or SEQ ID NO:3 can direct expression of an operably linked nucleic acid.

The term "percent sequence identity" refers to the degree of identity between any given query sequence, e.g., SEQ ID NO:1, and a subject sequence. A subject sequence typically has a length that is from 80 percent to 200 percent of the length of the query sequence, e.g., 82, 85, 87, 89, 90, 93, 95, 97, 99, 100, 105, 110, 115, 120, 130, 140, 150, 160, 170, 180, 190, or 200 percent of the length of the query sequence. A percent identity for any subject nucleic acid relative to a query nucleic acid can be determined as follows. A query nucleic acid sequence is aligned to one or more subject nucleic acid sequences using the computer program ClustalW (version 1.83, default parameters), which allows alignments of nucleic acid sequences to be carried out across their entire length (global alignment). Chema et al., *Nucleic Acids Res.*, 31(13): 3497-500 (2003).

ClustalW calculates the best match between a query and one or more subject sequences, and aligns them so that identities, similarities, and differences can be determined. Gaps of one or more residues can be inserted into a query sequence, a subject sequence, or both, to maximize sequence alignments. For fast pairwise alignment of nucleic acid sequences, the following parameters are used: word size: 2; window size: 4; scoring method: percentage; number of top diagonals: 4; and gap penalty: 5. For alignment of multiple nucleic acid sequences, the following parameters are used: gap opening penalty: 10.0; gap extension penalty: 5.0; and weight transitions: yes. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site (ebi.ac.uk/clustalw).

To determine the percent identity of a subject nucleic acid sequence to a query nucleic acid sequence, the sequences are aligned using ClustalW, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

A regulatory region featured herein can be made by cloning 5' flanking sequences of a HOMOLOGY-DEPENDENT GENE SILENCING 1 (HOG1) gene, an EMB2386 gene, or a gene encoding a putative elongation factor 2 polypeptide. Alternatively, a regulatory region can be made by chemical synthesis and/or PCR technology. PCR refers to a technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example, in *PCR Primer: A Laboratory Manual*, Ed. by Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplification. See, for example, Lewis, *Genetic Engineering News*, 12(9):1 (1992); Guatelli et al., *Proc. Natl. Acad. Sci. USA*, 87:1874-1878 (1990); and Weiss, Science, 254:1292 (1991). Various lengths of a regulatory region described herein can be made by similar techniques. A regulatory region also can be made by ligating together fragments of various regulatory regions. Methods for ligation of nucleic acid fragments, including PCR fragments, are known to those of ordinary skill in the art. PCR strategies also are available by which site-specific nucleotide sequence modifications can be introduced into a template nucleic acid.

The ability of a regulatory region to direct expression of an operably linked nucleic acid can be assayed using methods known to one having ordinary skill in the art. In particular, regulatory regions of varying lengths and regulatory regions comprising combinations of various regulatory regions ligated together can be operably linked to a reporter nucleic acid and used to transiently or stably transform a cell, e.g., a plant cell. Suitable reporter nucleic acids include β-glucuronidase (GUS), green fluorescent protein (GFP), yellow fluorescent protein (YFP), and luciferase (LUC). Expression of the gene product encoded by the reporter nucleic acid can be monitored in such transformed cells using standard techniques.

When a heterologous nucleic acid is operably linked to a broadly expressing regulatory region, transcription occurs in many, but not necessarily all, plant tissues. For example, a broadly expressing regulatory region can drive transcription in one or more of the flower, silique, ovule, stem, and root of a plant, but can drive transcription weakly or not at all in tissues such as shoot apical meristematic tissue. As another example, a broadly expressing regulatory region can drive transcription in one or more of the flower, silique, ovule, stem, leaf, and root of a plant, but can drive transcription weakly or not at all in stigma or pollen. A regulatory region described herein drives expression in various plant tissues, e.g., in flower, silique, stem, inflorescence, and root tissues as well as in the outer integument and endosperm of developing ovules and the seedling epidermis, cortex, and vasculature. Another regulatory region described herein directs transcription in various plant tissues including flower, silique, inflorescence, stem, leaf, and root tissues, as well as in the carpels, placentae, and developing seed coats of ovules and seeds in the siliques, and in the epidermis and root vasculature of the seedling. Another regulatory region described herein directs transcription in plant tissues such as the inflorescence, silique, root, stem, flower, leaf, outer integuments of pre-fertilization ovules and seed coats of developing and mature seeds, as well as in the epidermis, cortex, and vascular tissues of the seedling.

Nucleic Acid Constructs

Nucleic acid constructs containing nucleic acids such as those described herein also are provided. A nucleic acid construct can be a vector. A vector is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning, transformation, and expression vectors, as well as viral vectors and integrating vectors. An expression vector is a vector that includes one or more regulatory regions. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Mountain View, Calif.), Stratagene (La Jolla, Calif.), and Invitrogen/Life Technologies (Carlsbad, Calif.).

A nucleic acid construct includes a regulatory region as disclosed herein. A construct also can include a heterologous nucleic acid operably linked to the regulatory region, in which case the construct can be introduced into an organism and used to direct expression of the operably linked nucleic acid. The heterologous nucleic acid can be operably linked to the regulatory region in the sense or antisense orientation. In some embodiments, a heterologous nucleic acid is linked to a regulatory region in the sense orientation and transcribed and translated into a polypeptide. The regulatory region can be operably linked from approximately 1 to 150 nucleotides upstream of the ATG translation start codon of a heterologous nucleic acid in the sense orientation. For example, the regulatory region can be operably linked 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, 100 nucleotides, 110 nucleotides, 120 nucleotides, 130 nucleotides, 140 nucleotides, or 150 nucleotides upstream of the ATG translation start codon of a heterologous nucleic acid in the sense orientation. In some cases, the regulatory region can be operably linked from approximately 151 to 500 nucleotides upstream of the ATG translation start codon of a heterologous nucleic acid in the sense orientation. In some cases, the regulatory region can be operably linked from approximately 501 to 1125 nucleotides upstream of the ATG translation start codon of a heterologous nucleic acid in the sense orientation.

A nucleic acid construct can include a 3' untranslated region (3' UTR), which can increase stability of a transcribed sequence by providing for the addition of multiple adenylate ribonucleotides at the 3' end of the transcribed mRNA sequence. A 3' UTR can be, for example, the nopaline synthase (NOS) 3' UTR. A nucleic acid construct also can contain inducible elements, intron sequences, enhancer sequences, insulator sequences, or targeting sequences other than those present in a regulatory region described herein. Regulatory regions and other nucleic acids can be incorporated into a nucleic acid construct using methods known in the art.

A nucleic acid construct may contain more than one regulatory region. In some embodiments, each regulatory region is operably linked to a heterologous nucleic acid. For example, a nucleic acid construct may contain two regulatory regions, each operably linked to a different heterologous nucleic acid. The two regulatory regions can be the same or different, and one or both of the regulatory regions in such a construct can be a regulatory region described herein.

A nucleic acid construct may include a heterologous nucleic acid that is transcribed into an RNA useful for inhibiting expression of a gene. A number of nucleic acid based methods, including antisense RNA, ribozyme directed RNA cleavage, post-transcriptional gene silencing (PTGS), e.g., RNA interference (RNAi), and transcriptional gene silencing (TGS) can be used to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a heterologous nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophile*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the polypeptide of interest, and can have a length that is shorter, the same as, or longer than the corresponding length of the sense sequence. In some cases, one strand of the stem portion of a double stranded RNA comprises a sequence that is similar or identical to the 3' or 5' untranslated region of the mRNA encoding a polypeptide of interest, and the other strand of the stem portion of the double stranded RNA comprises a sequence that is similar or identical to the sequence that is complementary to the 3' or 5' untranslated region, respectively, of the mRNA encoding the polypeptide of interest. In other embodiments, one strand of the stem portion of a double stranded RNA comprises a sequence that is similar or identical to the sequence of an intron in the pre-mRNA encoding a polypeptide of interest, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a polypeptide of interest. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a heterologous nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a polypeptide of interest. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a polypeptide of interest. The sense sequence complementary to the antisense sequence can be a sequence present within the mRNA of the polypeptide of interest. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene.

Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region described herein to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141:1508-1518 (2006). The two regulatory regions can be the same or different. For example, any of the regulatory regions set forth in SEQ ID NOs:1-3, or any combination thereof, can be used. The two transcripts can form double-stranded RNA molecules that induce degradation of the target RNA. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

Transgenic Plants and Cells

Nucleic acids provided herein can be used to transform plant cells and generate transgenic plants. Thus, transgenic plants and plant cells containing the nucleic acids described herein also are provided, as are methods for making such transgenic plants and plant cells. A plant or plant cell can be transformed by having the construct integrated into its genome, i.e., can be stably transformed. Stably transformed cells typically retain the introduced nucleic acid sequence with each cell division. A plant or plant cell also can be transiently transformed such that the construct is not integrated into its genome. Transiently transformed cells typically lose some or all of the introduced nucleic acid construct with each cell division, such that the introduced nucleic acid cannot be detected in daughter cells after sufficient number of cell divisions. Both transiently transformed and stably transformed transgenic plants and plant cells can be useful in the methods described herein.

Transgenic plant cells used in the methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

As used herein, a transgenic plant also refers to progeny of an initial transgenic plant. Progeny include descendants of a particular plant or plant line. Progeny of an instant plant include seeds formed on $F_1$, $F_2$, $F_3$, $F_4$, $F_5$, $F_6$, and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$, and $F_6$ refer to subsequent generations of self- or sib-pollinated progeny of an $F_1$ plant. Seeds produced by a transgenic plant can be grown and then selfed (or outcrossed and selfed) to obtain plants and seeds homozygous for the nucleic acid construct. In some embodiments, transgenic plants exhibiting a desired trait are selected from among independent transformation events.

Transgenic plant cells can be grown in suspension culture, or tissue or organ culture. Solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880; 5,204,253; 5,591,616; and 6,329,571). If a cell or tissue culture is used as the recipient tissue for transformation, plants can be regenerated from transformed cultures using techniques known to those skilled in the art.

The polynucleotides and vectors described herein can be used to transform a number of monocotyledonous and dicotyledonous plants and plant cell systems, including dicots such as alfalfa, amaranth, apple, beans (including kidney beans, lima beans, green beans), broccoli, cabbage, carrot, castor bean, cherry, chick peas, chicory, clover, cocoa, coffee, cotton, cottonseed, crambe, eucalyptus, flax, grape, grapefruit, lemon, lentils, lettuce, linseed, mango, melon (e.g., watermelon, cantaloupe), mustard, orange, peach, peanut, pear, peas, pepper, plum, poplar, potato, rapeseed (high erucic acid and canola), safflower, sesame, soybean, spinach, strawberry, sugarbeet, sunflower, tea, tomato, as well as monocots such as banana, barley, date palm, field corn, garlic, millet, oat, oil palm, onion, pineapple, popcorn, rice, rye, sorghum, sudangrass, sugarcane, sweet corn, switchgrass, turf grasses, and wheat. Gymnosperms such as fir, pine and spruce can also be suitable.

Thus, the methods and compositions described herein can be used with dicotyledonous plants belonging, for example, to the orders Apiales, Arecales, Aristolochiales, Asterales, Batales, Campanulales, Capparales, Caryophyllales, Casuarinales, Celastrales, Cornales, Cucurbitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticales, and Violales. The methods and compositions described herein also can be utilized with monocotyledonous plants such as those belonging to the orders Alismatales, Arales, Arecales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales, and with plants belonging to Gymnospermae, e.g., Cycadales, Ginkgoales, Gnetales, and Pinales.

The methods and compositions can be used over a broad range of plant species, including species from the dicot genera *Arabidopsis, Brassica, Glycine, Gossypium, Helianthus, Jatropha, Lycopersicon, Medicago, Nicotiana, Petunia, Phaseolus, Pisum, Populus, Solanum*; and the monocot genera *Hordeum, Musa, Oryza, Panicum, Saccharum, Sorghum, Triticum*, and *Zea*; and the gymnosperm genera *Picea* and *Pinus*.

The polynucleotides and vectors described herein can be used to transform a number of monocotyledonous and dicotyledenous plants and plant cell systems, wherein such plants are hybrids of different species or varieties of a specific species (e.g., *Saccharum* sp. X *Miscanthus* sp.).

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, quantitative PCR, or reverse transcriptase PCR (RT-PCR) amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

A population of transgenic plants can be screened and/or selected for those members of the population that have a desired trait or phenotype conferred by expression of a nucleic acid operably linked to a regulatory region described herein. For example, a population of progeny of a single transformation event can be screened for those plants having a desired level of expression of a heterologous nucleic acid. As an alternative, a population of plants comprising independent transformation events can be screened for those plants having a desired level of expression of a heterologous nucleic acid. Selection and/or screening can be carried out over one or more generations, which can be useful to identify those plants that have a desired trait, such as an increased level of resistance to one or more pathogens. Selection and/or screening can also be carried out in more than one geographic location. In some cases, transgenic plants can be grown and selected under conditions which induce a desired phenotype or are otherwise necessary to produce a desired phenotype in a transgenic plant. In addition, selection and/or screening can be carried out during a particular developmental stage in which the phenotype is exhibited by the plant.

The phenotype of a transgenic plant or plant cell can be evaluated relative to a corresponding control plant or plant cell that either lacks the transgene or does not express the transgene. A corresponding control plant can be a corresponding wild-type plant, a corresponding plant that is not transgenic but otherwise is of the same genetic background as the transgenic plant of interest, or a corresponding plant of the same genetic background in which expression of the transgene is suppressed, inhibited, or not induced, e.g., where expression is under the control of an inducible promoter. A plant can be said "not to express" a transgene when the plant exhibits less than 10%, e.g., less than 9%, 8%, 7%, 6%, 5%, 4%, 3%, 2%, 1%, 0.5%, 0.1%, 0.01%, or 0.001%, of the amount of the polypeptide, mRNA encoding the polypeptide, or transcript of the transgene exhibited by the plant of interest. Expression can be evaluated using methods including, for example, quantitative PCR, RT-PCR, Northern blots, S1 RNase protection, primer extensions, Western blots, protein gel electrophoresis, immunoprecipitation, enzyme-linked immunoassays, microarray technology, and mass spectrometry. It should be noted that if a transgene is expressed under the control of a broadly expressing promoter, expression can be evaluated in a selected tissue or in the entire plant. Similarly, if a transgene is expressed at a particular time, e.g., at a particular time during development or upon induction, expression can be evaluated selectively during a desired time period.

A regulatory region disclosed herein can be used to express any of a number of heterologous nucleic acids of interest in a plant. For example, a regulatory region disclosed herein can be used to express a polypeptide or an interfering RNA. Suitable polypeptides include, without limitation, screenable and selectable markers such as green fluorescent protein, yellow fluorescent protein, luciferase, β-glucuronidase, or neomycin phosphotransferase II. Suitable polypeptides also include polypeptides that confer resistance to herbicides, antibiotics, insects, viruses, fungi, nematodes, or abiotic stress. Polypeptides involved in nutrient utilization, photosynthesis, senescence, or synthesis of proteins, sugars, or other compounds are also suitable, as are polypeptides that affect plant biomass, plant architecture, organ number, organ size, source strength, seed number, seed size, seed yield, flowering time, or flower number. In some embodiments, a heterologous nucleic acid encodes a polypeptide designated Clone 123905. See, U.S. Patent Publication 20060057724. In some embodiments, a heterologous nucleic acid encodes an enzyme involved in saccharide formation, e.g., levansucrase, dextransucrase, invertase, or sucrose phosphate synthase. In some embodiments, a heterologous polynucleotide encodes a non-plant polypeptide of pharmaceutical or industrial interest. In some embodiments, a heterologous nucleic acid encodes a polypeptide involved in pest defense, such as a *Bacillus thuringiensis* (Bt) insecticidal polypeptide. In some cases, a regulatory region disclosed herein can be used to express an interfering RNA that inhibits transcription of a senescence-associated gene, such as a SAG101 gene. In some cases, a regulatory region disclosed herein can be used to express a cyclin polypeptide, such as a cyclin polypeptide encoded by a CYC1 gene.

Use of a regulatory region provided herein to direct expression of a cyclin gene, such as a CYC1 gene, in a plant can increase the growth and yield of the plant compared to a corresponding wild-type plant. See, U.S. Pat. No. 6,252,139 and U.S. Pat. No. 6,696,623. In some embodiments, use of a regulatory region described herein to express in a plant a steroid receptor kinase, Bin1, which is involved in the pathway for synthesis of the plant brassinosteroid, brassinolide, can enhance disease resistance and increase plant yield, vegetative biomass, or seed yield compared to a corresponding wild-type plant. See, U.S. Pat. No. 6,245,969 and U.S. Pat. No. 6,765,085. In some embodiments, use of a regulatory region described herein to express a flavin-containing monooxygenase (FMO) gene, such as a YUCCA gene, in a plant can increase hypocotyl elongation, root thickness, root hair development, lateral root initiation, apical dominance, flowering node formation, fruit yield, and endogenous auxin levels compared to a corresponding control plant. See, U.S. Pat. No. 6,455,760. In some embodiments, use of a regulatory region provided herein to express in a plant a gene that is involved in the regulation of cell expansion (e.g., through effects on brassinosteroid response pathways), such as a Brassinazole Resistant 1 (BZR1) gene, may allow production of larger plants with higher crop yields compared to corresponding control crops. See, U.S. Patent Publication 20030150026. In some embodiments, use of a regulatory region provided herein to express a sucrose phosphate synthase polypeptide in a plant can increase the sweetness of the plant, or a product derived from the plant, compared to a corresponding control plant or product. In some embodiments, use of a regulatory region described herein to inhibit expression of a sucrose phosphate synthase gene can decrease the sweetness and caloric content of the plant or a product produced from the plant compared to a corresponding control plant or product. In some embodiments, use of materials and methods described herein to inhibit expression of a senescence-associated gene, such as a SAG101 gene, in a plant can delay the onset of senescence in the plant compared to a corresponding wild-type plant (He and Gan, *Plant Cell,* 14(4):805-15 (2002)).

In some embodiments, a regulatory region described herein can be used to express a gene involved in abscisic acid (ABA) biosynthesis, such as a NCED3 gene encoding a 9-cis-epoxycarotenoid dioxygenase (NCED) that catalyzes production of xanthoxin, a key intermediate in ABA biosynthesis. Use of a regulatory region described herein to express a NCED3 gene in a plant can alter the growth rate of the plant under a stressful environmental condition relative to a control plant. For example, such a transgenic plant can exhibit a greater rate of growth under drought conditions. In another example, such a transgenic plant can exhibit a greater rate of growth following re-hydration immediately preceded by drought. Thus, the physiological condition of a plant under drought conditions, or following drought and rehydration treatments can be a measure of its drought-recovery capability, and can be assessed with physiological parameters such as, for example, plant height, number of new shoots, number of new leaves, or seed number. When an NCED3 polypeptide is expressed in a transgenic plant, the transgenic plant can exhibit a greater height, a greater number of new shoots or new leaves, a greater number of seeds per plant, or an increase in seed weight per plant relative to a corresponding control plant. Transgenic plants also may exhibit a lower transpiration rate compared to control plants of the same genetic background. Transpiration rate is another physiological parameter that is indicative of how well a plant can tolerate drought conditions. For example, plants with a low transpiration rate are expected to lose water more slowly than plants with higher transpiration rates and therefore would be expected to better withstand drought conditions (i.e., have better drought tolerance).

In some embodiments, materials and methods described herein can be used to modulate expression in a plant of a gene involved in the biosynthesis of brassinosteroids, such as a gene encoding a cytochrome P450 polypeptide named CYP724B1. It has been suggested that the CYP724B1 polypeptide regulates the supply of 6-DeoxoTY and TY (Tanabe et al., *Plant Cell,* 17:776-790 (2005)). Use of materials and methods provided herein to inhibit expression of a gene encoding a CYP724B1 polypeptide in a plant, such as rice, can induce dwarfism. Compact or dwarf crop plants have many advantages in agriculture, including denser growth, increased resistance to storm damage, and reduced loss during harvesting. Alternatively, use of a regulatory region described herein to drive expression of a gene encoding a CYP724B1 polypeptide in a plant can enhance brassinosteroid biosynthesis and promote plant growth. Modulating expression of a gene encoding a CYP724B1 polypeptide in a plant also can allow the plant to grow in the dark without displaying mesocotyl or internode elongation characteristic of corresponding control plants.

In some embodiments, a regulatory region described herein can be used to drive the expression in a plant of a gene encoding a cytochrome P450 polypeptide, e.g., a 22-α-hydroxylase polypeptide that catalyzes the hydroxylation of campestanol at C-22 to produce 6-deoxocathasterone. See, U.S. Pat. No. 6,987,025 and U.S. Patent Publication 2006/0021089. Use of a regulatory region provided herein to express a 22-α-hydroxylase polypeptide in a transgenic plant can alter the metabolic profile of the transgenic plant. For example, a level of sucrose, glutamate, or linoleic acid in a transgenic plant expressing a 22-α-hydroxylase polypeptide can be higher than the corresponding level in a control plant. In some cases, a transgenic plant expressing a 22-α-hydroxylase polypeptide can exhibit an increased level of 6-deoxocathasterone and/or a decreased level of campestanol. In some cases, a transgenic plant expressing such a polypeptide can exhibit an increased photosynthetic rate or an accelerated growth rate at low temperatures or in dark conditions. In some cases, more than one phenotypic trait is modified, e.g., an increased level of 6-deoxocathasterone and a decreased level of campestanol. As a consequence of these altered phenotypic traits, transgenic plants can have improved growth potential with increased biomass, height, seed yield, seed weight, or improved seed fill.

The materials and methods described herein are useful for modifying biomass characteristics, such as characteristics of biomass renewable energy source plants. A biomass renewable energy source plant is a plant having or producing material (either raw or processed) that comprises stored solar energy that can be converted to fuel. In general terms, such plants comprise dedicated energy crops as well as agricultural and woody plants. Examples of biomass renewable energy source plants include: switchgrass, elephant grass, giant chinese silver grass, energycane, giant reed (also known as wild cane), tall fescue, bermuda grass, sorghum, napier grass (also known as uganda grass), triticale, rye, winter wheat, shrub poplar, shrub willow, big bluestem, reed canary grass, and corn.

Seeds of transgenic plants describe herein can be conditioned and bagged in packaging material by means known in the art to form an article of manufacture. Packaging material such as paper and cloth are well known in the art. Such a bag of seed preferably has a package label accompanying the bag, e.g., a tag or label secured to the packaging material, a label printed on the packaging material, or a label inserted within the bag.

The invention will be further described in the following examples, which do not limit the scope of the invention described in the claims.

EXAMPLES

Example 1

Characterizing the Expression Pattern of the PD1466 Regulatory Region

Sequence-specific primers were designed to amplify a 1000 base pair fragment of genomic DNA immediately upstream of the translation start site of the HOMOLOGY-DEPENDENT GENE SILENCING 1 (HOG1) gene of *Arabidopsis thaliana* ecotype Columbia. The HOG1 gene (locus tag At4g13940) codes for an S-adenosyl-L-homocysteine hydrolase polypeptide reported to be required for DNA methylation-dependent gene silencing. The primers were combined with genomic DNA from *Arabidopsis* to perform the polymerase chain reaction (PCR). The PCR product was designated PD1466. The predicted sequence of PD1466 is set forth in SEQ ID NO:1.

A linker sequence containing a Sfi I restriction endonuclease site was incorporated at both the 5' and the 3' ends of PD1466. Following restriction digestion, PD1466 was cloned into a cointegrate vector, CRS338-ERGFP, such that it was operably linked to a GFP gene. The GFP gene was optimized for expression in plants. See, U.S. Patent Publication No. 20050132432. The cointegrate vector construct also contained a phosphinotricin acetyltransferase gene that confers Finale™ resistance to transformed plants. Wild-type *Arabidopsis thaliana* ecotype Wassilewskija (Ws) plants were transformed with the cointegrate vector construct containing PD1466 essentially as described in Bechtold et al., *C.R. Acad. Sci. Paris,* 316:1194-1199 (1993).

Transgenic *Arabidopsis* plants transformed with the cointegrate vector construct containing PD1466 were analyzed for GFP expression. Mature $T_1$ plants, $T_2$ seedlings, and mature $T_2$ plants were evaluated. The plants were initially imaged using an inverted Leica DM IRB microscope. Two fluorescent filter blocks were used: (1) blue excitation BP 450-490 and long pass emission LP 515, and (2) green excitation BP 515-560 and long pass emission LP 590. The following objectives were used: HC PL FLUOTAR 5×/0.5, HCPL APO 10×/0.4 IMM water/glycerol/oil, HCPL APO 20×/0.7 IMM water/glycerol/oil, and HCXL APO 63×/1.2 IMM water/glycerol/oil. If expression was present, then imaging was performed using scanning laser confocal microscopy. A Leica TCS SP2 confocal scanner with detector optics having a spectral range of 400-850 nm was used with a variable computer controlled pinhole diameter, an optical zoom 1-32×, and four simultaneous detectors: three channels for collection of fluorescence or reflected light and one channel for detection of transmitted light. The laser sources were: (1) blue Ar 458/5 mW, 476 nm/5 mW, 488 nm/20 mW, 514 nm/20 mW, (2) green HeNe 543 nm/1.2 mW, and (3) red HeNe 633 nm/10 mW. Scanned images were taken as 2-D optical sections or 3-D images generated by stacking the 2-D optical sections collected in series. Tissues were dissected by eye or under magnification using INOX 5 grade forceps and placed on a slide with water and a coverslip. Efforts were made to record images of observed expression patterns at the earliest and latest stages of tissue development.

Mature $T_1$ plants from six independent transformation events with the PD1466 vector construct were analyzed for GFP expression. GFP expression was observed in transgenic plants from two of the events. A high intensity of GFP expression was observed throughout the inflorescence and developing flowers, siliques, ovules, and stems. GFP expression was also detected in the outer integument and endosperm of developing ovules.

More particularly, mature $T_1$ transgenic plants exhibited a high intensity of GFP expression in the pedicle, sepal, petal, filament, anther, carpel, epidermis, and silique of the flower. In the silique, a high intensity of GFP expression was also observed in the carpel and ovule. In the post-fertilization ovule, a high intensity of GFP expression was observed in the outer integument and seed coat. In addition, a high intensity of GFP expression was observed in the epidermis and vascular tissue of the stem as well as in the shoot apical meristem. Little or no GFP expression was observed in embryos and leaves of the $T_1$ plants.

$T_2$ seedlings from two independent transformation events with the PD1466 vector construct were analyzed for GFP expression. GFP expression was observed in plants from both events. A high intensity of GFP expression was observed throughout the epidermis, cortex, and vasculature of the transgenic $T_2$ seedlings.

More particularly, the transgenic seedlings exhibited a high intensity of GFP expression in the epidermis, cortex, and vascular tissue of the hypocotyl. A high intensity of GFP expression was also observed in the epidermis of the cotyledon. In the primary root, a high intensity of GFP expression was observed in the cortex and the root cap, whereas a low intensity of GFP expression was observed in the epidermis and the root hairs. GFP expression was also observed in the shoot apical meristem. Little or no expression of GFP was observed in rosette leaves and lateral roots of the transgenic $T_2$ seedlings.

Mature $T_2$ plants transformed with the PD1466 vector construct were also analyzed for GFP expression. Expression of GFP was observed in $T_2$ plants from three out of the six events analyzed. A high intensity of GFP expression was observed throughout the flowers, siliques, stems, and primary roots of the mature $T_2$ plants. GFP expression was also observed in the shoot apical meristem. Little or no expression of GFP was detected in rosette leaves and lateral roots of the transgenic $T_2$ plants.

Example 2

Characterizing the Expression Pattern of the PD1468 Regulatory Region

Sequence-specific primers were designed to amplify a 1000 base pair fragment of genomic DNA immediately upstream of the translation start site of the EMB2386 gene of *Arabidopsis thaliana* ecotype Columbia. The EMB2386 gene (locus tag At1g02780) encodes a 60S ribosomal protein L19 (RPL19A) polypeptide annotated as a structural constituent of a ribosome. The primers were combined with genomic DNA from *Arabidopsis* to perform PCR. The PCR product was designated PD1468. The predicted sequence of PD1468 is set forth in SEQ ID NO:2.

A linker sequence containing a Sfi I restriction endonuclease site was incorporated at both the 5' and the 3' end of PD1468. Following restriction digestion, PD1468 was cloned into a cointegrate vector, CRS338-ERGFP, such that it was operably linked to a GFP gene. The GFP gene was optimized for expression in plants. See, U.S. Patent Publication No. 20050132432. The cointegrate vector construct also contained a phosphinotricin acetyltransferase gene that confers Finale™ resistance to transformed plants. Wild-type *Arabidopsis thaliana* ecotype Ws plants were transformed with the cointegrate vector construct containing PD1468 essentially as described in Bechtold et al., *C. R. Acad. Sci. Paris*, 316: 1194-1199 (1993).

Transgenic *Arabidopsis* plants transformed with the cointegrate vector construct containing PD1468 were analyzed for GFP expression as described in Example 1 above. Mature $T_1$ plants, $T_2$ seedlings, and mature $T_2$ plants were evaluated.

GFP expression was observed in mature $T_1$ transgenic plants from two out of six events analyzed. The intensity of GFP expression was high in the inflorescence, stems, and siliques as well as in the carpels, placenta, and developing seed coats of ovules and seeds in the siliques. A high intensity of GFP expression was also observed throughout the stems, leaves, and roots.

More particularly, mature $T_1$ transgenic plants exhibited a high intensity of GFP expression in the pedicle, carpel, and silique of the flower, and a low intensity of GFP expression in the sepal of the flower. In the silique, a high intensity of GFP expression was detected in the carpel, septum, placenta, funiculus, epidermis, abscission zone, and ovule. The intensity of GFP expression was high in the outer integument and funiculus of the pre-fertilization ovule, as well as in the outer integument and developing seed coat of the post-fertilization ovule. The intensity of GFP expression was also high in the root, and in the epidermis, cortex, interfascicular region, vascular tissue, xylem, phloem, and pith of the stem. In the leaf, a high intensity of GFP expression was observed in the epidermis, while a low intensity of GFP expression was observed in the mesophyll and vascular tissue. Little or no GFP expression was detected in the stigma and pollen of the $T_1$ plants.

$T_2$ seedlings from two out of six independent transformation events with the PD1468 vector construct exhibited GFP expression. A low intensity of GFP expression was observed throughout the seedling epidermis and root vasculature. A high intensity of GFP expression was observed in the epidermis of the hypocotyls as well as in the epidermis and mesophyll of the cotyledon. In the primary root, the intensity of GFP expression was high in the root cap and low in the epidermis and vascular tissue. In the lateral root, the intensity of GFP expression was high in the primordia. Little or no GFP expression was detected in the shoot apical meristems of the $T_2$ seedlings.

Mature $T_2$ plants from two independent transformation events with the PD1468 vector were analyzed for GFP expression, and expression of GFP was observed in plants from both events. The intensity of GFP expression was high in the inflorescence, siliques, flowers, and roots of the transgenic $T_2$ plants.

Example 3

Characterizing the Expression Pattern of the PD1485 Regulatory Region

A predicted regulatory region from the putative elongation factor 2 (EF-2) gene of *Arabidopsis thaliana* ecotype Columbia was amplified using PCR. The putative EF-2 gene (locus tag At1g56070) encodes a translation elongation factor 2-like polypeptide that is reported to be involved in cold-induced translation. Sequence-specific primers were used to amplify a 997 base pair fragment of genomic DNA immediately upstream of the translation start site of the putative EF-2 gene. The 997 base pair fragment was designated PD1485 (SEQ ID NO:3).

A linker sequence containing a Sfi I restriction endonuclease site was incorporated at both the 5' and the 3' end of PD1485. Following restriction digestion with Sfi I, PD1485 was cloned into a cointegrate vector, CRS338-ERGFP, such that it was operably linked to a GFP gene. The GFP gene was optimized for expression in plants. See, U.S. Patent Publication No. 20050132432. The cointegrate vector construct also contained a phosphinotricin acetyltransferase gene that confers Finale™ resistance to transformed plants. Wild-type *Arabidopsis thaliana* ecotype Ws plants were transformed with the cointegrate vector construct containing PD1485 essentially as described in Bechtold et al., *C. R. Acad. Sci. Paris*, 316:1194-1199 (1993).

The in planta nucleotide sequence of PD1485 in mature $T_1$ plants was confirmed by DNA sequencing in one direction. The sequence of PD1485 in $T_2$ plants from two or three events was confirmed by DNA sequencing in both directions. The sequence of PD1485 in $T_1$ and $T_2$ plants matched the *Arabidopsis* genome sequence.

Transgenic *Arabidopsis* plants transformed with the cointegrate vector construct containing PD1485 were analyzed for GFP expression as described in Example 1 above. Mature $T_1$ plants, $T_2$ seedlings, and mature $T_2$ plants were evaluated.

Expression of GFP was observed in $T_1$ transgenic plants from four out of five events analyzed. The intensity of the GFP expression was high in the inflorescence, stems, leaves, and flowers. The intensity of the GFP expression was high throughout the flower, including the embryo and pollen. A high intensity of GFP expression was also observed in the outer integuments of pre-fertilization ovules and seed coats of developing and mature seeds.

More particularly, T₁ transgenic plants exhibited a high intensity of GFP expression in the pedicel, receptacle, nectary, sepal, petal, filament, pollen, carpel, style, papillae, vascular tissue, epidermis, and silique of the flower. In the silique, the intensity of GFP expression was high in the stigma, style, carpel, septum, placenta, funiculus, epidermis, abscission zone, and ovule. In the pre-fertilization ovule, the intensity of GFP expression was high in the outer integument, funiculus, chalaza, and micropyle. In the post-fertilization ovule, the intensity of GFP expression was high in the funiculus and outer integument. A high intensity of GFP expression was also observed in the seed coats of developing and mature seeds, and in the torpedo of the embryo. The expression of GFP was high throughout the stem, i.e., in the epidermis, cortex, interfascicular region, vascular tissue, xylem, phloem, pith, stomata, and trichome. In the leaf, a high intensity of GFP expression was likewise observed in the petiole, mesophyll, vascular tissue, epidermis, and trichome. Little or no GFP expression was detected in the shoot apical meristem.

T₂ seedlings from three out of four independent transformation events with the PD1485 construct exhibited GFP expression. The intensity of GFP expression was high throughout the epidermis, cortex, and vascular tissue. More particularly, a high intensity of GFP expression was observed in the epidermis and vascular tissue of the hypocotyl; in the epidermis and mesophyll of the cotyledon; in the epidermis, cortex, vascular tissue, and root cap of the primary root; and in the shoot apical meristem. Little or no GFP expression was detected in the lateral root.

Mature T₂ plants from two independent transformation events with the PD1485 vector construct were analyzed for GFP expression, and GFP was detected in plants from both events. The intensity of GFP expression was high in the inflorescence, flowers, siliques, and roots of the transgenic T₂ plants.

Transgenic *Arabidopsis* plants from three independent transformation events with the PD1485 construct were analyzed for GFP transcript levels using quantitative PCR. Plants were grown hydroponically for four weeks. Rosette leaves, flowers, siliques, stems, and roots were harvested separately for analysis. The GFP transcript level expressed under the direction of the PD1485 regulatory region in each tissue type was compared to the GFP transcript level expressed with the CaMV 35S promoter in the same tissue type. Levels of GFP transcripts obtained using the PD1485 regulatory region were expressed as a percentage of the corresponding levels of GFP transcripts obtained with the CaMV 35S promoter (Table 1).

TABLE 1

Level of GFP expression directed by the PD1485 regulatory region relative to the level of GFP expression directed by the CaMV 35S promoter in various tissue types

|  | Roots | Rosette Leaves | Flowers | Siliques | Stems |
| --- | --- | --- | --- | --- | --- |
| Event-01 | 5.968 | 17.678 | 11.663 | 10.633 | 4.847 |
| Event-03 | 5.698 | 32.234 | 10.882 | 6.396 | 4.029 |
| Event-04 | 2.849 | 19.843 | 9.257 | 5.018 | 2.368 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid construct comprising a regulatory region operably linked to a heterologous polynucleotide, said regulatory region comprising a) the polynucleotide sequence set forth in SEQ ID NO:2 or SEQ ID NO:3, or b) a fragment of the polynucleotide sequence set forth in SEQ ID NO:2 or SEQ ID NO:3 that is at least 80% of the length of SEQ ID NO:2 or SEQ ID NO:3, wherein said regulatory region directs transcription of said operably linked heterologous polynucleotide in a tissue selected from the group consisting of flower, silique, and root tissue.

2. The nucleic acid construct of claim 1, wherein said nucleic acid construct comprises a regulatory region having a nucleotide sequence corresponding to SEQ ID NO:2.

3. The nucleic acid construct of claim 1, wherein said nucleic acid construct comprises a regulatory region having a nucleotide sequence corresponding to SEQ ID NO:3.

4. The nucleic acid construct of claim 1, wherein said heterologous polynucleotide comprises a polynucleotide sequence encoding a polypeptide.

5. The nucleic acid construct of claim 1, wherein said heterologous polynucleotide is in an antisense orientation relative to said regulatory region.

6. The nucleic acid construct of claim 1, wherein said heterologous polynucleotide is transcribed into an RNA that inhibits expression of a gene.

7. A transgenic plant or plant cell transformed with the nucleic acid construct of claim 1.

8. A method of producing a transgenic plant, said method comprising (a) introducing into a plant cell an isolated polynucleotide comprising the nucleic acid construct of claim 1, and (b) growing a plant from said plant cell.

* * * * *